United States Patent
Stasiak et al.

(10) Patent No.: US 6,294,525 B1
(45) Date of Patent: Sep. 25, 2001

(54) REVERSE-TURN MIMETICS AND METHODS RELATING THERETO

(75) Inventors: Marcin Stasiak; Michael Kahn, both of Kirkland, WA (US)

(73) Assignee: Molecumetics Ltd., Bellevue, WA (US)

( * ) Notice: Subject to any disclaimer, the term of this patent is extended or adjusted under 35 U.S.C. 154(b) by 0 days.

(21) Appl. No.: 09/388,854

(22) Filed: Sep. 1, 1999

(51) Int. Cl.$^7$ .......................... A61K 21/33; A61K 31/55; A61K 38/12; C07D 281/18; C07D 487/00

(52) U.S. Cl. .......................... 514/183; 514/221; 514/249; 530/317; 530/323; 530/333; 540/469; 540/502; 544/236

(58) Field of Search .................................. 540/469, 502; 544/236; 514/221, 183, 249; 530/317, 323, 333

(56) References Cited

U.S. PATENT DOCUMENTS

| | | | |
|---|---|---|---|
| 5,440,013 | 8/1995 | Kahn | 530/317 |
| 5,545,568 | 8/1996 | Ellman | 436/518 |
| 5,929,237 | 7/1999 | Kahn | 544/279 |
| 6,013,458 | 1/2000 | Kahn et al. | 435/7.1 |

FOREIGN PATENT DOCUMENTS

| | | |
|---|---|---|
| WO 94/03494 | 2/1994 | (WO) . |
| WO 97/15557 | 5/1997 | (WO) . |

OTHER PUBLICATIONS

Lucente, Chemical Abstracts 89:110346, abstract of Tetrahedron Lett, vol. 11, pp 1009–1012, 1978.*
Hackh's Chemical Dictionary, Grang, Julius (editor), pp. 332,532 and 656, 1944.*
Abignente et al., "Research on heterocyclic compounds. XVI. 2–Methylimidazo[1,2–a]pyrazine–3–carboxylic acids," *Chemical Abstracts Database*, Accession No. 103:87841, 1985.
Barrow and Sun, "Spiroquinazoline, a novel substance P inhibitor with a new carbon skeleton, isolated from Aspergillus flavipes," *Chemical Abstracts Database*, Accession No. 121:129499, 1994.
Cutler et al., "Cinereain: a novel metabolite with plant growth regulating properties from *Botrytis cinerea*," *Chemical Abstracts Database*, Accession No. 109:165645, 1988.
Dennin et al., "Synthesis of derivatives of pyrazino[1,2–a]pyrimidin–4–ones," *Chemical Abstracts Database*, Accession No. 114: 164135, 1991.
Faehnle and Rothe, "Synthese and reactions of peptide cyclols," *Chemical Abstracts Database*, Accession No. 102:7061, 1985.
Gatta et al., "New [f]–fused xanthines: synthesis of 1,3–dipropyl–1H, 3H–pyrazino, pyrido, pyrimido and Pyrrolo [2,1–f]purine–2,4–diones," *Chemical Abstracts Database*: 121:57444, 1994.

Kadam et al., "Fermentative Manufacture of Multiple drug resistance–attenuating ardeemins," *Chemical Abstracts Marpat Database*, Accession No. 121:7435, 1994.
Kappe and Kappe, "Cross–conjugated and pseudo–cross–conjugated mesomeric betaines. XVIII. Bicyclic mesoionic pyrimidines with cardiovascular activity," *Chemical Abstracts Database*, Accession No. 116:83634, 1992.
Lam et al., "A new type of synthetic peptide library for identifying ligand–binding activity," *Nature* 354: 82–84, 1991.
Lucente et al., "Synthesis and x–ray crystal structure of a tripeptidic cyclol," *Chemical Abstracts Database*, Accession No. 96:69410, 1982.
Numata et al., "Structures of cytotoxic substances and new quinazoline derivatives produced by a fungus from a saltwater fish," *Chemical Abstracts Database*, Accession No. 166:210833, 1992.
Okawara et al., "Preparation and hydrogenolysis of fused piperazines by reaction of diamine and triamine derivatives with benzil. Applications to the synthesis of terminal N–monoprotected triamines," *Chemical Abstracts Database*, Accession No. 117:191810, 1992.
Okawara et al., "Simple preparation of terminal N–monoprotected triamines using fused piperazines," *Chemical Abstracts Database*, Accession No. 114:101300, 1991.
Penn et al., "Biosynthesis of glyantrypine by Aspergillus clavatus," *Chemical Abstracts Database*, Accession No. 117:44249, 1992.
Penn et al., "Glyantrypine, a novel anthranilic acid–containing metabolite of Aspergillus clavatus," *Chemical Abstracts Database*, Accession No. 117:127875, 1992.

(List continued on next page.)

Primary Examiner—D. Margaret Seaman
(74) *Attorney, Agent, or Firm*—Seed Intellectual Property Law Group PLLC

(57) ABSTRACT

Conformationally constrained compounds which mimic the secondary structure of reverse-turn regions of biologically active peptides and proteins having the following structure are disclosed:

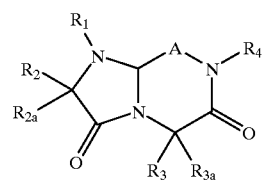

wherein A, $R_1$, $R_2$, $R_{2a}$, $R_3$, $R_{3a}$ and $R_4$ are as defined herein. Such compounds have utility over a wide range of fields, including use as diagnostic and therapeutic agents. In particular, compounds of this invention are useful in pharmaceutical compositions as anti-inflammatory agents. Libraries containing the compounds of this invention are also disclosed, as well as methods for screening the same to identify biologically active members.

24 Claims, No Drawings

OTHER PUBLICATIONS

Pinnen et al., "Cyclization under mild conditions of anthraniloyl and N–methlanthraniloyl dipeptides," *Chemical Abstracts Database*, Accession No. 110:76029, 1989.

Pinnen et al., "Ten–membered cyclotripeptides: influence of the ring–flexibility on intramolecular reactions," *Chemical Abstracts Database*, Accession No. 102:132448, 1985.

Rothe et al., "Cyclol formation during tripeptide cyclizations. Synthesis of a secondary cyclotripeptide, cyclo–(D–Phe–L–Pro–L–Pro)," *Chemical Abstracts Database*, Accession No. 97:56231, 1982.

Rothe et al., "Secondary all–L–cyclotripeptides," *Chemical Abstracts Database*, Accession No. 103:215766, 1985.

Sauter et al., "Novel basically substituted pyrimidines and benzothienopyrimidines," *Chemical Abstracts Database*, Accession No. 87:84931, 1977.

Tanaka and Narita, "Syntheses of pyrido[2,3–b]pyrazine derivatives," *Chemical Abstracts Database*, Accession No. 84:31002, 1976.

Vojkovsky et al., "Solid–Phase Synthesis of Heterocycles Containing an 1–Acyl–3–oxopiperazine Skeleton," *J. Org. Chem.* 63: 3162–3163, 1998.

* cited by examiner

REVERSE-TURN MIMETICS AND METHODS RELATING THERETO

TECHNICAL FIELD

The present invention relates generally to reverse-turn mimetics, including inhibitors of cell adhesion-mediated disease, as well as to a chemical library of reverse-turn mimetics.

BACKGROUND OF THE INVENTION

In the search for new therapeutics, the pharmaceutical industry has increasingly turned to the techniques of combinatorial chemistry, parallel synthesis, and high throughput screening to generate and optimize lead compounds (*Combinatorial Chemistry and Molecular Diversity in Drug Discovery* Gordon and Kerwin, Eds., John Wiley & Sons, New York, 1998; *The Combinatorial Index* Bunin, Academic Press, New York, 1998; *A Practical Guide to Combinatorial Chemistry* Czarnik and DeWitt, Eds., American Chemical Society, Washington, D.C., 1997; *High Throughput Screening: The Discovery of Bioactive Substances* Devlin, Marcel Dekker, New York, 1997). These techniques can produce libraries of hundreds to hundreds of thousands—or more—of compounds in a short period of time. The libraries are then assayed against targets of interest, often in a highly automated fashion, to identify biologically active compounds. Libraries, which are simply collections of compounds, may be tightly focused around a specific template or contain a variety of unrelated templates. In many instances, the diversity of the library is an important design parameter.

On a basic level, the number of points of diversity on a molecular template or scaffold, i.e., the number of positions at which variation in structure may be introduced, has a practical effect on the ease with which large libraries may be created. When combinatorial techniques are employed, a template that contains three points of diversity would give rise to 8000 compounds if 20 components are used to derivatize each point and a total of 60 reactions are carried out ($20^3$). However, a template with four points of diversity will yield over 50,000 compounds when 15 components are used at each point in a total of 60 reactions ($15^4$). In general, large libraries may be created more efficiently on templates allowing more possibilities for derivatization.

In order to increase the chances of finding a biologically active compound for a particular target, it is usually desirable to synthesize a library spanning a range of both conformational space and chemical properties such as hydrophobicity and hydrogen bonding ability. At the same time, low molecular weight is often a goal as well, since compounds of less than 500 Daltons are perceived as more likely to have favorable pharmacokinetic properties in relation to higher molecular weight compounds. All these characteristics point to the continuing need for small compact templates that support a wide range of substituents and which are simple to synthesize.

Reverse-turns comprise one of three classes of protein secondary structure and display three (gamma-turn), four (beta-turns), or more (loops) amino acid side chains in a fixed spatial relationship to each other. Turns have proven important in molecular recognition events (Rose et al., *Advances in Protein Chemistry* 37:1–109, 1985) and have engendered a burgeoning field of research into small molecule mimetics of them (e.g., Hanessian et al., *Tetrahedron* 53:12789–12854, 1997). Many mimetics have either been external turn-mimetics which do not allow for the display of all the physiologically relevant side-chains (e.g., Freidinger et al., *Science* 210:656–8, 1980) or small, conformationally mobile cyclic peptide derivatives (e.g., Viles et al., *Eur. J Biochem.* 242:352–62, 1996). However, non-peptide compounds have been developed which closely mimic the secondary structure of reverse-turns found in biologically active proteins or peptides. For example, U.S. Pat. Nos. 5,475,085, 5,670,155 and 5,672,681 to Kahn and published PCT WO94/03494 to Kahn all disclose conformationally constrained, non-peptidic compounds which mimic the three-dimensional structure of reverse-turns. More recently, U.S. Pat. No. 5,929,237 to Kahn, and published PCT WO97/15577 to Kahn and PCT WO98/49168 to Kahn et al. disclosed additional, highly constrained bicyclic heterocycles as reverse-turn mimetics. Nevertheless, as no one template can mimic every type of turn, there remains a need in the art for additional reverse-turn templates.

Cell adhesion is critical to the viability of living organisms. Adhesion holds multicellular tissues together and directs embryonic development. It plays important roles in wound healing, eradication of infection and blood coagulation. Integrins are a family of cell surface proteins intimately involved in all of these functions. They have been found in nearly every type of human cell except red blood cells. Abnormalities in integrin function contribute to a variety of disorders including inflammatory diseases, heart attack, stroke, and cancer.

Integrins consist of heterodimers of $\alpha$ and $\beta$ subunits, non-covalently bound to each other. These cell surface receptors extend through the cell membrane into the cytoplasm. At least 15 different $\alpha$ and 9 different $\beta$ subunits are known. However, because most $\alpha$ proteins associate with only a single $\beta$ there are about 21 known integrin receptors. On the cell surface the heads of the two subunits contact each other to form a binding surface for extracellular protein ligands, allowing attachment to other cells or to the extracellular matrix. The affinity of these receptors may be regulated by signals from outside or within the cell. For example, recruitment of leukocytes to the site of injury or infection involves a series of adhesive interactions. Weak interaction between endothelial and leukocyte selectins and carbohydrates mediate transient adhesion and rolling of the leukocyte along the vessel wall. Various chemokines and other trigger factors released by the site of inflammation serve as signals to activate integrins from a quiescent to a high affinity state. These activated integrins then bind their cognate ligands on the surface of the endothelial cells, resulting in strong adhesion and flattening of the leukocyte. Subsequently the leukocyte migrates through the endothelium into the tissue below.

Integrin $\alpha_4\beta_1$ mediates cell adhesion primarily through binding to either vascular cell adhesion molecule-1 (VCAM-1) or an alternatively spliced variant of fibronectin containing the type III connecting segment (IIICS). A variety of cells involved in inflammation express $\alpha_4\beta_1$, including lymphocytes, monocytes, basophils and eosinophils, but not neutrophils. Monoclonal antibodies to the $\alpha_4$ subunit have been used to validate $\alpha_4$-containing integrins as potential therapeutic targets in animal models of rheumatoid arthritis (Barbadillo et al., *Springer Semin Immunopathol.* 16:427–36, 1995; Issekutz et al., *Immunology* 88:569–76, 1996), acute colitis (Podolsky et al., *J Clin. Invest.* 92:372–80, 1993), multiple sclerosis (Yednock et al., *Nature* 356:63–6, 1992), asthma (Abraham et al., *J Clin. Invest.* 93:776–87, 1994) U.S. Pat. No. 5,871,734) and diabetes (Tsukamoto et al., *Cell Immunol.* 165:193–201, 1995). More recently, low molecular weight peptidyl derivatives have been produced as competitive inhibitors of $\alpha_4\beta_1$ and one has been shown to inhibit allergic airway responses in sheep (Lin et al., *J Med. Chem.* 42:920–34, 1999).

It has been shown that a key sequence in IIICS involved in binding to $\alpha_4\beta_1$ is the 25 residue peptide CS1, and within that sequence the minimally recognized motif is the tripeptide, LDV. A similar sequence, IDS, has been implicated in the binding of VCAM-1 to $\alpha_4\beta_1$. X-ray crystal structures of an N-terminal two-domain fragment of VCAM-1 show that the IDS sequence is part of an exposed loop linking two beta-strands (Jones et al., *Nature* 373:539–44, 1995; Wang et al., *Proc. Natl. Acad. Sci. USA* 92:5714–8, 1995). Cyclic peptides and derivatives thereof which adopt reverse-turn conformations have proven to be inhibitors of VCAM-1 binding to $\alpha_4\beta_1$ (WO 96/00581; WO 96/06108; Doyle et al., *Int. J Pept. Protein Res.* 47:427–36, 1996). In addition, a number of potent and selective (versus $\alpha_4\beta_1$) cyclic peptide-based inhibitors have been discovered (Jackson et al., *J Med. Chem.* 40:3359–68, 1997). Several non-peptidyl beta-turn mimetics have also been reported to bind $\alpha_4\beta_1$ with $IC_{50}$s in the low micromolar range (Souers et al., *Bioorg. Med. Chem. Lett.* 8:2297–302, 1998). Numerous phenylalanine and tyrosine derivatives have also been disclosed as inhibitors of $\alpha_4\beta_1$ (WO 99/06390; WO 99/06431; WO 99/06433; WO 99/06434; WO 99/06435; WO 99/06436; WO 99/06437; WO 98/54207; WO 99/10312; WO 99/10313; WO 98/53814; WO 98/53817; WO 98/58902). However, no potent and orally available small molecule inhibitors have been disclosed.

A related integrin, $\alpha_4\beta_7$, is expressed on the surface of lymphocytes and binds VCAM-1, fibronectin and mucosal addressin cell adhesion molecule 1 (MAdCAM-1). Integrin $\alpha_4\beta_7$ and MAdCAM mediate recirculation of a subset of lymphocytes between the blood, gut, and lymphoid tissue. Similar to VCAM-1 and Fibronectin CS-1 there is a tripeptide sequence, LDT, present on the CD loop of MAdCAM-1 which is important for recognition by $\alpha_4\beta_7$. An X-ray crystal structure shows this sequence is also part of a turn structure (Tan et al., *Structure* 6:793–801, 1998). Recent studies have shown that $\alpha_4\beta_7$ may also play a part in diseases such as asthma (Lobb et al., *Ann. NYA cad. Sci.* 796:113–23, 1996), inflammatory bowel disease (Fong et al., *Immunol. Res.* 16:299–311, 1997), and diabetes (Yang et al., *Diabetes* 46:1542–7, 1997). In addition, while $\alpha_4$ integrins appear to be down-regulated in carcinomas such as cervical and prostate, they appear to be up-regulated in metastatic melanoma (Sanders et al., *Cancer Invest.* 16:329–44, 1998), suggesting that inhibitors of $\alpha_4\beta_1$ and $\alpha_4\beta_7$ may be useful as anticancer agents.

While significant advances have been made in the synthesis and identification of conformationally constrained, reverse-turn mimetics, there is still a need in the art for small molecules that mimic the secondary structure of peptides. There is also a need in the art for libraries containing such members, particularly those small templates capable of supporting a high diversity of substituents. In addition, there is a need in the art for techniques for synthesizing these libraries and screening the library members against biological targets to identify bioactive library members. Further, there is a need in the art for small, orally available inhibitors of integrins, for use in treating inflammatory diseases and cardiovascular diseases, as well as some cancers. In particular there is a need for inhibitors of $\alpha_4\beta_1$ and $\alpha_4\beta_7$, for use in the treatment of rheumatoid arthritis, asthma, diabetes and inflammatory bowel disease.

The present invention fulfills these needs, and provides further related advantages.

SUMMARY OF THE INVENTION

In brief, the present invention is directed to conformationally constrained compounds which mimic the secondary structure of reverse-turn regions of biologically active peptides and proteins (also referred to herein as "reverse-turn mimetics"). The compounds of the present invention have the following general structure (I):

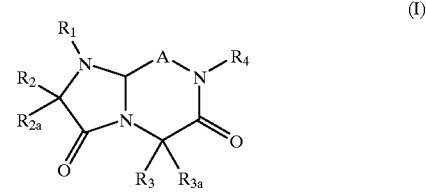

including pharmaceutically acceptable salts and stereoisomers thereof, wherein A and $R_1$ through $R_4$ are as defined below.

The present invention is also directed to libraries containing compounds of structure (I), as well as methods for synthesizing such libraries and methods for screening the same to identify biologically active compounds. In addition, compositions containing a compound of this invention in combination with a pharmaceutically acceptable carrier are disclosed. Methods of use for treating cell-adhesion-mediated disease with the compounds of this invention and compositions comprising them are also disclosed.

These and other aspects of this invention will be apparent upon reference to the following detailed description. To this end, various references are set forth herein which describe in more detail certain procedures, compounds and/or compositions, and are incorporated by reference in their entirety.

DETAILED DESCRIPTION OF THE INVENTION

The present invention is directed to reverse-turn mimetics and chemical libraries containing reverse-turn mimetics. The reverse-turn mimetics of the present invention are useful as bioactive agents, including (but not limited to) use as diagnostic, prophylactic and/or therapeutic agents, especially as anti-inflammatory agents. The reverse-turn mimetic libraries of this invention are useful in the identification of such bioactive agents. In the practice of the present invention, the libraries may contain from tens to hundreds to thousands (or greater) of individual reverse-turn mimetics (also referred to herein as "members").

In one aspect of the present invention, a reverse-turn mimetic is disclosed having the following structure (I):

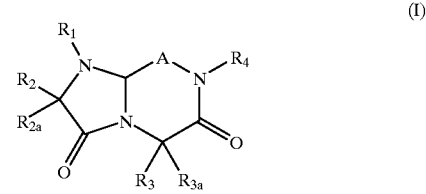

and pharmaceutically acceptable salts and stereoisomers thereof,
wherein
A is $-(CR_5R_{5a})_n-$ where n is 1, 2 or 3;
$R_2$, $R_3$ and $R_5$ are, at each occurrence, the same or different and independently an amino acid side chain moiety or amino acid side chain derivative, a peptide or peptide derivative, a linker or a solid support;

$R_{2a}$, $R_{3a}$ and $R_{5a}$ are, at each occurrence, the same or different and independently hydrogen, hydroxy, —COOH, —CONH$_2$, —R$_6$, —OR$_6$, —COOR$_6$, —COR$_6$ or —CONHR6, where R$_6$ is lower alkyl optionally substituted with halogen or hydroxy; and $R_1$ and $R_4$ represent the remainder of the molecule, with the proviso that when $R_1$ is —C(=O)OMe and $R_4$ is benzyl, $R_2$ is not isopropyl when $R_3$ is methyl and $R_2$ is not methyl when $R_3$ is isopropyl.

As used herein, an "amino acid side chain moiety" represents any amino acid side chain moiety present in naturally occurring proteins including (but not limited to) the naturally occurring amino acid side chain moieties identified in Table 1 below. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

AMINO ACID SIDE CHAIN MOIETIES

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_2$ | Lysine |
| —(CH$_2$)$_3$NHC(NH$_2$)NH$_2$ | Arginine |
| 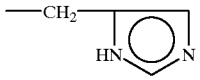 | Histidine |
| —CH$_2$COOH | Aspartic acid |
| —CH$_2$CH$_2$COOH | Glutamic acid |
| —CH$_2$CONH$_2$ | Asparagine |
| —CH$_2$CH$_2$CONH$_2$ | Glutamine |
| 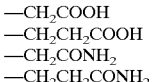 | Phenylalanine |
| 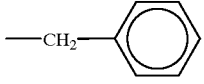 | Tyrosine |
| 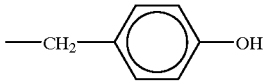 | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| 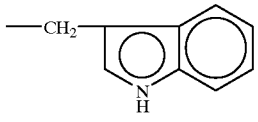 | Proline |

TABLE 1-continued

AMINO ACID SIDE CHAIN MOIETIES

| Amino Acid Side Chain Moiety | Amino Acid |
|---|---|
| 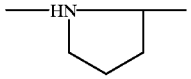 | Hydroxyproline |

In addition, as used herein, an "amino acid side chain derivative" represents modifications and/or variations to naturally occurring amino acid side chain moieties. For example, the amino acid side chain moieties of alanine, valine, leucine, isoleucine and phenylalanine may generally be classified as alkyl, aryl, or arylalkyl moieties, optionally substituted with one or more substituents as defined below. Accordingly, representative amino acid side chain derivatives include substituted or unsubstituted alkyl, aryl and arylalkyl moieties.

To this end, "alkyl" is a straight chain or branched, cyclic or noncyclic, saturated or unsaturated alkyl containing from 1 to 12 carbon atoms (also referred to herein as "$C_{1-12}$alkyl"). Similarly, a "lower alkyl" is as defined above, but contains from 1 to 4 carbon atoms (also referred to herein as a "$C_{1-4}$alkyl"). Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-i butynyl, and the like. Representative unsaturated cyclic alkyls include cyclopentenyl and cyclohexenyl, and the like.

"Aryl" is an aromatic carbocyclic moiety contain from 6 to 12 carbon atoms (also referred to herein as a "$C_{6-12}$aryl"), such as phenyl and naphthyl.

"Arylalkyl" is an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

Similarly, the amino acid side chain moieties of histidine, tryptophan, proline and hydroxyproline may generally be classified as heterocyclic or heterocyclicalkyl moieties, optionally substituted with one or more substituents as defined below. Accordingly, representative amino acid side chain derivatives also include substituted or unsubstituted heterocycle and heterocylealkyl moieties.

As used herein, "heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Thus, in addition to the heteroaryls listed below, heterocycles also include morpholinyl, pyrrolidinonyl, pyrrolidinyl, piperidinyl, hydantoinyl, valerolactamyl, oxiranyl, oxetanyl, aziridinyl, azetidinyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle moiety, such as —$CH_2$(heterocycle), —$(CH_2)_2$(heterocycle), and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

The term "substituted" as used herein means any of the above groups—that is, alkyl, aryl, arylalkyl, heterocycle, heterocyclealkyl, heteroaryl or heteroarylalkyl—wherein at least one hydrogen atom is replaced with a substituent. In the case of a keto substituent ("C(=O)") two hydrogen atoms are replaced. A "substituent" in this regard is halogen, keto, hydroxy, haloalkyl, —R, —OR, —C(=O)R, —C(=O)OR, —C(=O)NRR, —NRR, —NRC(=O)R, —NRC(=O)OR, —NRC(=O)NRR, —OC(=O)R, —OC(=O)OR, —OC(=O)NRR, —SH, —SR, —SOR, —$SO_2$R, —$NRSO_2$R, —$SiR_3$, or —$OP(OR)_3$, wherein each occurrence of R is the same or different and independently hydrogen, alkyl, aryl, arylalkyl, heterocycle or heterocyclealkyl, or wherein any two R groups attached to the same nitrogen atom, taken together with the nitrogen atom to which they are attached, form a heterocyclic ring or a substituted heterocyclic ring.

A "peptide" means at least two naturally or unnaturally occurring alpha-amino acids joined via a peptide bond. Depending upon the number of amino acids joined via peptide bonds, the resulting peptide may also be referred to as a "polypeptide" or "protein." Similarly, a "peptide derivative" means a peptide which has been covalently modified and/or which contains amino acids other than alpha-amino acids. Representative peptide derivatives include peptides which are N-alkylated, N-acylated or N-sulfonylated at the amino tennini, with, for example, methyl, benzyl, acetyl, benzoyl, methanesulfonyl, phenylsulfonyl, allyloxycarbonyl, t-butyloxycarbonyl, benzyloxycarbonyl, or fluorenyloxycarbonyl moieties; peptides in which the carboxy termini are esterified (methyl, ethyl, benzyl) or reduced to a hydroxy or aldehyde; peptides which are N-alkylated at peptide bonds with, for example, methyl or 2-hydroxy-4-methoxybenzyl; and peptides which incorporate beta- or gamma-amino acids such as beta-alanine or gamma-aminobutyric acid.

A "linker" is any covalent bridging moiety that facilitates linkage of a compound of structure (I), through the respective $R_1$, $R_2$, $R_3$, $R_4$ and/or $R_5$ moiety, to another moiety, agent, compound, solid support, molecule, amino acid, peptide or protein. For example, the compounds of this invention may be linked to one or more known compounds, such as biotin, for use in diagnostic or screening assays. Furthermore, one (or more) of $R_1$, $R_2$, $R_3$, $R_4$ or $R_5$ may be a linker joining the compound of structure (I) to a solid support (such as a support used in solid phase peptide synthesis). Examples of such linkers include p-alkoxybenzyl alcohol, phenylacetamidomethyl, and 2-chlorotrityl chloride. In this context, linkage to another moiety or compound, or to a solid support, is preferable at the $R_1$ or $R_4$ position.

A "solid support" means any composition of matter to which another compound is attached directly or attached through a linker and which is insoluble in at least one solvent that the attached compound is soluble in. Alternatively, a "solid support" may be a composition of matter with similar solubility characteristics to the attached compound, but which may be readily precipitated from solution and filtered off as a solid. Representative examples include polystyrene, polyethylene glycol, polystyrene grafted with polyethylene glycol, polyacrylamide, polyamide-polyethylene glycol copolymer, controlled-pore glass, and silica.

The phrase "remainder of the molecule" means any moiety, agent, compound, solid support, molecule, linker, amino acid, peptide or protein covalently attached to the reverse-turn mimetic at either the $R_1$ and/or $R_4$ positions, including amino acid side chain moieties, amino acid side chain derivatives and peptide derivatives as defined above. Accordingly, an alternative depiction of structure (I), the bond between the ring nitrogen atoms and the corresponding $R_1$ and $R_4$ moieties may be left undefined, as represented by the following structure (I'):

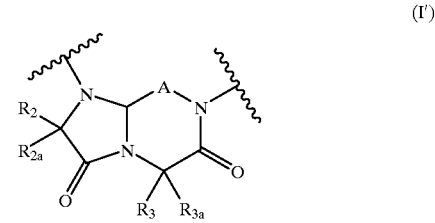

(I')

wherein "〰〰〰〰" represents the remainder of the molecule joined to the corresponding ring nitrogen through a covalent bond, and A, $R_2$ and $R_3$ are as defined above.

In an embodiment of structure (I), $R_{2a}$, $R_{3a}$ and each occurrence of $R_{5a}$ and $R_5$ are hydrogen, and the compounds of this invention have the following structure (II):

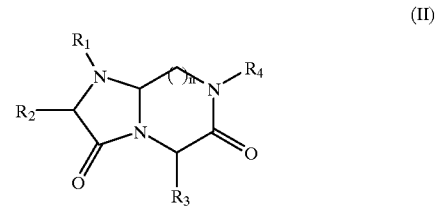

(II)

wherein n, $R_1$, $R_2$, $R_3$ and $R_4$ are as defined above.

In another embodiment, A is —$CH(R_5)CH(R_5)$—, $R_{2a}$ and $R_{3a}$ are both hydrogen, and the compounds of this invention have the following structure (III):

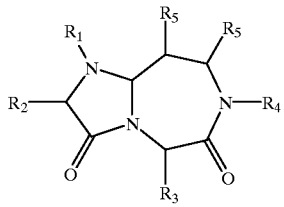

(III)

wherein $R_1$, $R_2$, $R_3$, $R_4$ and each occurrence of $R_5$ are as defined above.

In still a further embodiment, n is 1, $R_{2a}$, $R_{3a}$ and $R_{5a}$ are hydrogen, and the compounds of this invention have the following structure (IV):

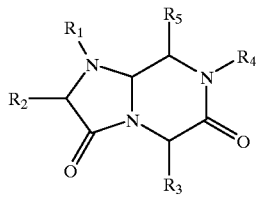

(IV)

wherein $R_1$, $R_2$, $R_3$, $R_4$ and $R_5$ are as defined above.

In a more specific embodiment of structure (IV), $R_5$ is hydrogen and the compounds of this invention have the following structure (V):

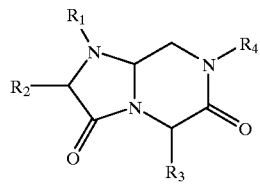

(V)

wherein $R_1$, $R_2$, $R_3$ and $R_4$ are as defined above.

In yet another embodiment of structure (I), $R_{3a}$ is hydrogen, and the compounds of this invention have the following structure (VI):

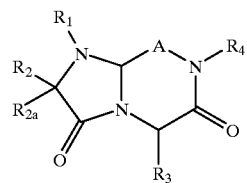

(VI)

wherein A, $R_1$, $R_2$, $R_{2a}$, $R_3$ and $R_4$ are as defined above.

In a preferred embodiment of structure (I), $R_{2a}$, $R_{3a}$ and each occurrence of $R_{5a}$ are hydrogen, $R_1$, $R_2$, $R_3$ and $R_4$ are the same or different and independently an amino acid side chain moiety or amino acid side chain derivative. In a further preferred embodiment of structure (I), $R_1$ is —C(=O)O$R_7$, —C(=O)NH$R_7$ or —SO$_2$$R_7$, where $R_7$ is an amino acid side chain moiety or an amino acid side chain derivative. In still a further preferred embodiment of structure, $R_7$ is aryl or arylalkyl optionally substituted with halogen, —OH, —COOH, —NH$_2$ or $C_{1-4}$alkyl.

In structure (I) above, a solid line designation for attachment of the various R groups to a carbon atom on the fused bicyclic ring indicates that these R groups may lie either above or below the plane of the page. If a reverse-turn mimetic of this invention is intended to mimic a reverse-turn of naturally occurring amino acids (i.e., "L-amino acids"), the R groups would generally lie below the plane of the page (i.e., "⋯⋯⋯⋅⋅⋅{R") in Structure (I). However, if the reverse-turn mimetic of this invention is intended to mimic a reverse-turn containing one or more D-amino acids, then the corresponding R group or groups would lie above the plane of the page (i.e., "▬▬▬R") in Structure (I).

The reverse-turn mimetics of the present invention may generally be prepared by the method illustrated in the following Reaction Scheme.

Reaction Scheme

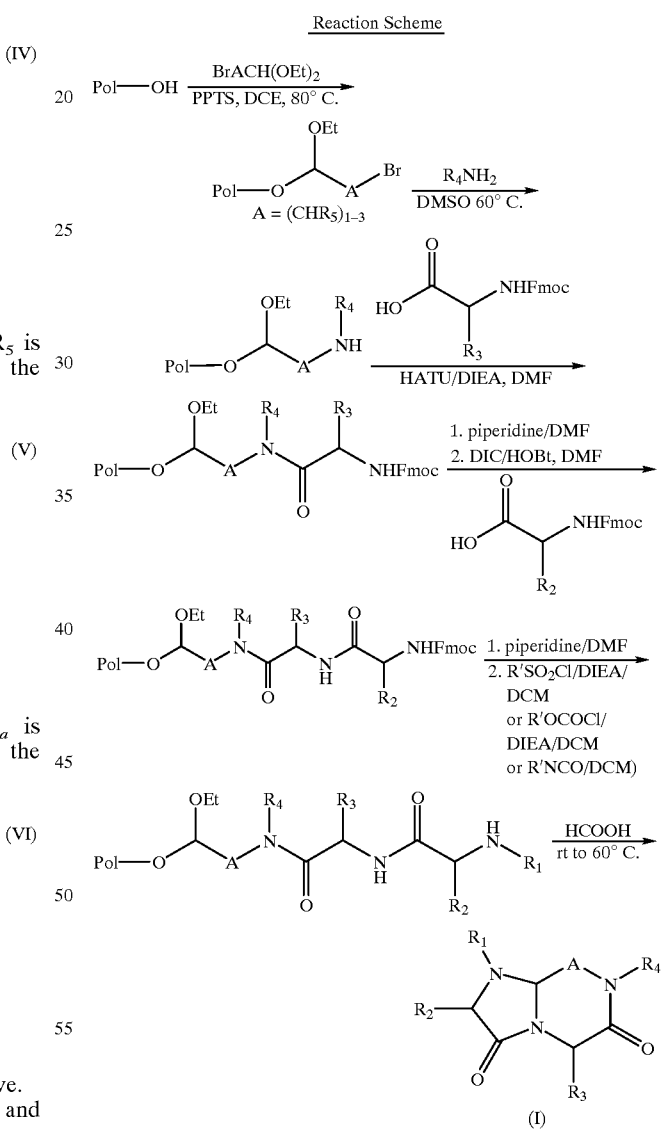

In the above Reaction Scheme, a resin bearing free hydroxyl groups is treated with a bromine-containing acetal under acidic conditions. The derivatized resin is reacted with a primary amine and subsequently acylated with an N-protected amino acid derivative in the presence of a coupling reagent and base. The amino protection is removed and a second N-protected amino acid derivative is coupled.

After deprotection, the exposed primary amine is capped with a suitable reagent such as a sulfonyl chloride, chloroformate, or isocyanate. The compound is simultaneously removed from the resin and cyclized to form the final product by treatment with formic acid. Alternatively, the reverse-turn mimetics of structure (I) may be prepared in solution by sequential or convergent coupling of the individual components.

While the above Reaction Scheme depicts the $R_{2a}$ and $R_{3a}$ moieties as hydrogen, compounds of structure (I) having moieties other than hydrogen at the $R_{2a}$ and $R_{3a}$ position may be made by the same Reaction Scheme, but using the corresponding $R_{2a}$-substituted and/or $R_{3a}$-substituted reaction precursors. For example, when $R_2$ and $R_{2a}$ are both methyl, a suitable aminoisobutyric acid derivative may be used to introduce these groups into the reverse-turn mimetic.

As mentioned above, the reverse-turn mimetics of the present invention are useful as bio-active agents, such as diagnostic, prophylactic, and therapeutic agents. The integrin binding activity of representative reverse-turn mimetics is presented in Example 2. In this example, the reverse-turn mimetics were found to effectively displace CS1 peptide from Ramos cells. The data thus indicate the ability of reverse turn mimetics to antagonize $\alpha_4\beta_1$ integrins and serve as potential anti-inflammatory agents.

In another aspect of this invention, libraries containing reverse-turn mimetics of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields reverse-turn mimetics which are themselves biologically active, and thus useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the component pieces of this invention. More specifically, any amino acid sequence may be added as any of the $R_1$, $R_2$, $R_3$, $R_4$ or $R_5$ moieties of the conformationally constrained reverse-turn mimetic. Preferably the amino acid sequence may be added as the $R_1$ or $R_4$ moieties. To this end, the mimetics may be synthesized on a solid support (such as polystyrene utilizing 4-hydroxymethylphenoxybutyrate as a linker) by known techniques (see, e.g., John M. Stewart and Janis D. Young, *Solid Phase Peptide Synthesis*, 1984, Pierce Chemical Comp., Rockford, Ill.; Atherton, E., Shepard, R. C. *Solid Phase Peptide Synthesis: A Practical Approach*; IRL: Oxford, 1989) or on a silyl-linked resin by alcohol attachment (see Randolph et al., *J Am. Chem. Soc.* 117:5712–14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. A suitable conformationally constrained reverse-turn mimetic which has been previously synthesized by solution synthesis techniques may then be added as the next "amino acid" to the solid phase synthesis (i.e., the conformationally constrained reverse-turn mimetic, which has at least two reactive sites, may be utilized as the next residue to be added to the linear peptide). Upon incorporation of the conformationally constrained reverse-turn mimetic into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic in solution using known solution coupling techniques.

In another aspect of this invention, methods for constructing the libraries are disclosed. Traditional combinatorial chemistry (see, e.g., The *Combinatorial Index* Bunin, Academic Press, New York, 1998; Gallop et al., *J Med. Chem.* 37:1233–1251, 1994) and parallel synthesis techniques permit a vast number of compounds to be rapidly prepared by the sequential combination of reagents to a basic molecular scaffold. For example, the above disclosed synthesis may be carried out using the directed sorting technique of Nicolaou and coworkers. (Nicolaou et al., *Angew. Chem. Int'l.* Ed. 34:2289–2291, 1995). Presently, equipment for this technique is commercially available from IRORI (La Jolla, Calif.). Alternatively, the above disclosed synthesis may be carried out by parallel synthesis using a 48- or 98-well plate format wherein each well contains a fritted outlet for draining solvents and reagents (*A Practical Guide to Combinatorial Chemistry* Czarnik and DeWitt, Eds., American Chemical Society, Washington, D.C., 1997). Robbins (Sunnyvale, Calif.), Charybdis (Carlsbad, Calif.) and Bohdan (Chicago, Ill.) presently offer suitable equipment for this technique.

In a further aspect of this invention, methods for screening the libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the colorimetric assay disclosed by Lam et al. (*Nature* 354:82–84, 1991) or Griminski et al. (*Biotechnology* 12:1008–1011, 1994). In a preferred embodiment, the library members are in solution and the target is immobilized on a solid phase. Alternatively, the library may be immobilized on a solid phase and may be probed by contacting it with the target in solution.

In another aspect, the present invention encompasses pharmaceutical compositions prepared for storage or administration which comprise a therapeutically effective amount of a compound of the present invention in a pharmaceutically acceptable carrier or diluent. Therapy with inhibitors of cell adhesion is indicated for the treatment and prevention of a variety of inflammatory conditions, particularly rheumatoid arthritis, inflammatory bowel disease and asthma. Those experienced in this field are readily aware of the circumstances requiring anti-inflammatory therapy.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use, including diluents, are well known in the pharmaceutical art, and are described, for example, in *Remingtons Pharmaceutical Sciences*, Mack Publishing Co. (Gennaro Ed. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

Compounds of the present invention are useful for prevention and treatment of any condition in which an excess of integrin-mediated cell adhesion is a contributing factor. In particular, the compounds of the present invention are useful as agents for the prevention and treatment of inflammation. In the practice of the methods of this invention, a composition containing a therapeutically effective amount of a compound of this invention is administered to a warm-blooded animal in need thereof. For example, the compounds of this invention may be administered to a warm-blooded animal that has been diagnosed with, or is at risk of developing a condition selected from rheumatoid arthritis, atherosclerosis, Alzheimer's disease, AIDS dementia, ARDS, asthma, allergies, inflammatory bowel disease, CNS inflammation, atopic dermatitis, type I diabetes, encephalitis, myocardial ischemia, multiple sclerosis, meningitis, nephritis, reperfusion injury, restenosis, retinitis, psoriasis, stroke and tumor metastasis.

Multiple sclerosis (MS) is a progressively debilitating autoimmune disease of the central nervous system. Presently the exact antigen triggering the immune response is unknown. However, macrophages appear to attack and initiate the destruction of the fatty myelin sheaths surrounding nerve fibers in the brain. In an animal model of MS (experimental allergic encephalomyelitis) murine monoclonal antibodies to $\alpha_4\beta_1$ blocked adhesion of the leukocytes to the endothelium, and prevented inflammation of the central nervous system and subsequent paralysis of the animals (Yednock, Cannon et al., *Nature* 356: 63–6, 1992).

The compounds of the present invention may be used singularly, as a combination of two or more compounds, or in combination with other known inhibitors of inflammation. For example the compounds of this invention may be used therapeutically with corticosteroids, non-steroidal anti-inflammatory agents, COX-2 inhibitors, matrix metalloprotease inhibitors or lipoxygenase inhibitors. The compounds of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, intranasal, intrarectal or intramuscular form, all using forms well known to those of ordinary skill in the pharmaceutical arts. The compounds may be administered intraocularly or topically as well as orally or parenterally.

The compounds of this invention may be administered by inhalation, and thus may be delivered in the form of an aerosol spray from pressurized packs or nebulizers. The compounds may also be delivered as powders which may be formulated and the powder composition may be inhaled with the aid of an insufflation powder inhaler device. A preferred delivery system for inhalation is the metered dose inhalation aerosol, which may be formulated as a suspension or solution of a compound of the invention in suitable propellants, such as fluorocarbons or hydrocarbons. Another preferred delivery system is the dry powder inhalation aerosol, which may be formulated as a dry powder of a compound of this invention with or without additional excipients.

The compounds of the invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of this invention may also be delivered by the use of monoclonal antibodies as individual carriers to which the compound molecules are coupled. The integrin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartarnide-phenol, or polyethyleneoxide-polylysine substituted with palmitoyl residues. Furthermore, the integrin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dose and method of administration can be tailored to achieve optimal efficacy but will depend on such factors as weight, diet, concurrent medication and other factors which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

Tablets suitable for oral administration of active compounds of the invention can be prepared as follows:

|  | Amount-mg | | |
| --- | --- | --- | --- |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

An intravenous dosage form of the above-indicated active compounds may be prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopoeia/National Formulary for 1995, published by United States Pharmacopoeia Convention, Inc., Rockville, Md., copyright 1994).

The following examples are provided for purposes of illustration, not limitation.

EXAMPLES

Example 1
Synthesis os Representative Compounds of Structure (I)

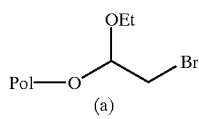
(a)

In general, a batch of resin (ArgogelOH or hydroxymethyl polystyrene) was refluxed in 1,2-dichloroethane (DCE) for 4 hours in the presence of 8 equivalents of bromoalkylaldehyde diethyl acetal and 2 equivalents of pyridinium p-toluenesulfonate (PPTS). In one instance, hydroxymethyl polystyrene (10.0 g, 0.7 mmol OH/g, 7 mmol) and 3.5 g of PPTS (14 mmol) were suspended in 200 ml of DCE. Then, a solution of 8.5 ml of 2-bromodiethoxyethane (ca. 56 mmol) in DCE (100 ml) was added with stirring and the reaction mixture was heated at reflux (approx. 80° C). After 4 hours the resin was filtered off and washed with 100 mL dimethylformamide (DMF), 50 mL dimethylsulfoxide (DMSO), 100 mL DMF, 200 mL dichloromethane (DCM), 50 mL 1,4-dioxane and finally with 100 mL methanol. After drying, 11.73 g, of resin (a) was obtained. Bromine analysis indicated quantitative loading.

Synthesis of Representative Compounds

Reactions were carried out in plastic disposable syringes of the appropriate size, each fitted with a polypropylene frit to retain the resin. After each step, resin batches were washed with DMF (3×) and DCM (3×). Typically, a 0.03 mmol sample of resin (a) (e.g., 50 mg of polystyrene resin with loading of 0.6 mmol Br/g), pre-swollen in DMF, was treated with 1 mL of a 2.0 M solution of amine $R_4$—$NH_2$ (2 mmol) in DMSO at 60° C. for 16–24 hrs.

Next, the resin was reacted with 0.09 mmol of Fmoc amino acid (FmocNH—$CHR_3$—COOH) in the presence of HATU (34 mg, 0.09 mmol) and DIEA (0.032 ml, 0.18 mmol) in DMF (1 mL) until the chloranil test was negative (typically 1–2 h). Subsequently, the Fmoc protection was removed by treatment with a 25% (v/v) piperidine/DMF solution (2 mL) over 20 min.

The resin was then reacted with 0.09 mmol of a second Fmoc amino acid (FmocNH—$CHR_2$—COOH) in the presence of DIC (0.014 ml, 0.09 mmol) and HOBt (14 mg, 0.09 mmol) in DMF (1 mL) until the Kaiser test was negative (typically 1 hour). The resin was again treated with 25% (v/v) piperidine/DMF solution (2 mL) over 20 mm.

Finally, the resin-bound sequence was terminated by reaction with sulfonyl chloride ($R_1SO_2Cl$, 0.3 mmol) in the presence of DIEA (0.106 mL, 0.6 mmol) in DCM (1 mL) for 1 hr (Kaiser test negative). Alternatively, chloroformate $R_1OCOCl$ or isocyanate R1NCO (the latter does not require presence of DIEA) was used instead of sulfonyl chloride for introduction of the $R_1$ moiety.

The washed and dried resin was re-swollen in DCM, drained and treated with 1 mL of formic acid (96%) overnight at rt. In a number of cases, an elevated temperature up to 60° C. or an extended reaction time was necessary to complete the cyclization (for conditions see Table 2 below). The supernatant was collected and combined with washes (2×0.5 mL of formic acid). The residue obtained after evaporation of formic acid was redissolved in acetonitrile/water 50:50 mixture, frozen and lyophilized. The yields of crude material were 85–100%. The crude purity of compounds bearing a sulfonyl moiety at $R_1$ generally exceeded 80%.

Table 2 presents representative compounds of this invention synthesized by the above procedure.

TABLE 2

REPRESENTATIVE COMPOUNDS)

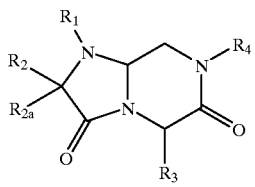

| Cpd. No. | R₁ | R₂ | R₂ₐ | R₃ | R₄ | Cleavage Conditions | LC RT‡ (min) | MS (M + H⁺) |
|---|---|---|---|---|---|---|---|---|
| 1 | PhNH-C(O)-X₁ | H₃C""X₂ | H-X₂ₐ | X₃-CH₂CH(CH₃)₂ | 4-MeO-C₆H₄-CH₂-X₄ | rt | 3.56(A) | 465.5 |
| 2 | 4-Me-C₆H₄-SO₂-X₁ | H₃C""X₂ | H-X₂ₐ | X₃-CH₂-Ph | (CH₃)₂CH-CH₂-X₄ | rt | 3.77(A) | 470.5 |
| 3 | Fmoc-X₁ | (CH₃)₂CH-CH₂-X₂ | H""X₂ₐ | X₃-CH₃ | Ph-CH₂-X₄ | rt | 4.01(A) | 538.6 |
| 4 | 4-Me-C₆H₄-SO₂-X₁ | HOOC-CH₂-""X₂ | H-X₂ₐ | X₃-CH₂-C₆H₄-4-OH | X₄-CH₂-COOH | rt | 6.40(A) | 532.3 |
| 5 | 2-naphthyl-SO₂-X₁ | HOOC-CH₂-""X₂ | H-X₂ₐ | X₃-CH₂-C₆H₄-4-OH | X₄-CH₂-COOH | rt | 7.26(B) | 568.3 |
| 6 | 4-Me-C₆H₄-SO₂-X₁ | HOOC-CH₂-""X₂ | H""X₂ₐ | X₃-CH₂-C₆H₄-4-OH | X₄-CH₂-COOH | rt | 7.04(B) | 532.3 |

TABLE 2-continued

REPRESENTATIVE COMPOUNDS)

| Cpd. No. | $R_1$ | $R_2$ | $R_{2a}$ | $R_3$ | $R_4$ | Cleavage Conditions | LC RT‡ (min) | MS (M + H⁺) |
|---|---|---|---|---|---|---|---|---|
| 7 | naphthalene-2-sulfonyl | CH₂COOH (X₂) | H (X₂ₐ) | 4-hydroxybenzyl (X₃) | CH₂COOH (X₄) | rt | 7.78(B) | 568.3 |
| 8 | naphthalene-1-sulfonyl | CH₂COOH (X₂) | H (X₂ₐ) | 4-hydroxybenzyl (X₃) | isobutyl (X₄) | 40° C. | 2.64(C) | 580.5 |
| 9 | 4-chlorobenzenesulfonyl | CH₂COOH (X₂) | H (X₂ₐ) | 4-hydroxybenzyl (X₃) | isobutyl (X₄) | 40° C. | 2.58(C) | 564.4 |
| 10 | 4-chlorobenzenesulfonyl | CH₂COOH (X₂) | H (X₂ₐ) | 4-hydroxybenzyl (X₃) | isobutyl (X₄) | 40° C. | 2.67(C) | 550.4 |
| 11 | 4-methylbenzenesulfonyl | CH₂COOH (X₂) | H (X₂ₐ) | 4-hydroxybenzyl (X₃) | isobutyl (X₄) | 40° C. | 2.27(C) | 468.4 |
| 12 | naphthalene-2-sulfonyl | isobutyl (X₂) | H (X₂ₐ) | CH₂COOH (X₃) | isobutyl (X₄) | rt | 1.64(D) | 516.7 |
| 13 | Fmoc | H₃C (X₂) | H₃C (X₂) | CH₂COOH (X₃) | isobutyl (X₄) | rt | 1.54(D) | 520.8 |

TABLE 2-continued

REPRESENTATIVE COMPOUNDS)

| Cpd. No. | R$_1$ | R$_2$ | R$_{2a}$ | R$_3$ | R$_4$ | Cleavage Conditions | LC RT‡ (min) | MS (M + H$^+$) |
|---|---|---|---|---|---|---|---|---|
| 14 | 2-naphthyl-SO$_2$-X$_1$ | H$_3$C''''X$_2$ | H$_3$C-X$_{2a}$ | X$_3$-CH$_2$-COOH | (CH$_3$)$_2$CHCH$_2$-X$_4$ | rt | 1.52(D) | 488.7 |
| 15 | 2-naphthyl-SO$_2$-X$_1$ | (H$_3$C)$_2$CH-X$_2$ | H-X$_{2a}$ | X$_3$-CH$_2$-COOH | (CH$_3$)$_2$CHCH$_2$-X$_4$ | 40° C. | 1.58(D) | 502.8 |
| 16 | 2-naphthyl-SO$_2$-X$_1$ | H$_3$CCH$_2$(H$_3$C)CH-X$_2$ | H-X$_{2a}$ | X$_3$-CH$_2$-COOH | (CH$_3$)$_2$CHCH$_2$-X$_4$ | 40° C. | 1.60(D) | 516.8 |
| 17 | styryl-SO$_2$-X$_1$ | HOOC-CH$_2$-X$_2$ | H-X$_{2a}$ | X$_3$-CH(CH$_3$)$_2$ | (CH$_3$)$_2$CHCH$_2$-X$_4$ | rt | 1.45(D) | 478.3 |
| 18 | styryl-SO$_2$-X$_1$ | HOOC-CH$_2$-X$_2$ | H-X$_{2a}$ | X$_3$-CH(CH$_3$)$_2$ | PhCH$_2$-X$_4$ | rt | 1.47(D) | 512.3 |
| 19 | 1-naphthyl-SO$_2$-X$_1$ | HOOC-CH$_2$CH$_2$-X$_2$ | H-X$_{2a}$ | X$_3$-CH(CH$_3$)$_2$ | (CH$_3$)$_2$CHCH$_2$-X$_4$ | 40° C. | 1.50(D) | 516.3 |
| 20 | 2-naphthyl-SO$_2$-X$_1$ | HOOC-CH$_2$CH$_2$-X$_2$ | H-X$_{2a}$ | X$_3$-CH(CH$_3$)$_2$ | (CH$_3$)$_2$CHCH$_2$-X$_4$ | 40° C. | 1.55(D) | 516.3 |
| 21 | 4-Cl-C$_6$H$_4$-SO$_2$-X$_1$ | HOOC-CH$_2$CH$_2$-X$_2$ | H-X$_{2a}$ | X$_3$-CH(CH$_3$)$_2$ | (CH$_3$)$_2$CHCH$_2$-X$_4$ | 40° C. | 1.51(D) | 499.3 |

TABLE 2-continued

REPRESENTATIVE COMPOUNDS)

| Cpd. No. | R₁ | R₂ | R₂ₐ | R₃ | R₄ | Cleavage Conditions | LC RT‡ (min) | MS (M + H⁺) |
|---|---|---|---|---|---|---|---|---|
| 22 | 4-iodophenylsulfonyl (X₁) | -CH₂CH₂COOH (X₂) | H (X₂ₐ) | isopropyl (X₃) | isobutyl (X₄) | 40° C. | 1.55(D) | 592.4 |
| 23 | (E)-styrylsulfonyl (X₁) | -CH₂CH₂COOH (X₂) | H (X₂ₐ) | isopropyl (X₃) | isobutyl (X₄) | 40° C. | 1.48(D) | 492.4 |
| 24 | quinolin-8-ylsulfonyl (X₁) | -CH₂CH₂COOH (X₂) | H (X₂ₐ) | isopropyl (X₃) | isobutyl (X₄) | 40° C. | 1.38(D) | 517.4 |
| 25 | naphthalen-1-ylsulfonyl (X₁) | -CH₂CH₂COOH (X₂) | H (X₂ₐ) | isopropyl (X₃) | benzyl (X₄) | 40° C. | 1.54(D) | 550.5 |
| 26 | naphthalen-2-ylsulfonyl (X₁) | -CH₂CH₂COOH (X₂) | H (X₂ₐ) | isopropyl (X₃) | benzyl (X₄) | 40° C. | 1.58(D) | 550.5 |
| 27 | 4-chlorophenylsulfonyl (X₁) | -CH₂CH₂COOH (X₂) | H (X₂ₐ) | isopropyl (X₃) | benzyl (X₄) | 40° C. | 1.52(D) | 533.2 |
| 28 | 4-iodophenylsulfonyl (X₁) | -CH₂CH₂COOH (X₂) | H (X₂ₐ) | isopropyl (X₃) | benzyl (X₄) | 40° C. | 1.57(D) | 626.2 |

TABLE 2-continued

REPRESENTATIVE COMPOUNDS)

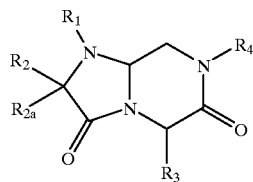

| Cpd. No. | R₁ | R₂ | R₂ₐ | R₃ | R₄ | Cleavage Conditions | LC RT‡ (min) | MS (M + H⁺) |
|---|---|---|---|---|---|---|---|---|
| 29 | (E)-styrylsulfonyl-X₁ | -CH₂CH₂COOH, X₂ | H-X₂ₐ | isopropyl, X₃ | benzyl, X₄ | 40° C. | 1.52(D) | 526.5 |
| 30 | quinolin-8-ylsulfonyl-X₁ | -CH₂CH₂COOH, X₂ | H-X₂ₐ | isopropyl, X₃ | benzyl, X₄ | 40° C. | 1.42(D) | 551.4 |
| 31 | 4-chlorophenylsulfonyl-X₁ | -CH₂CH₂COOH, X₂ | H-X₂ₐ | isobutyl, X₃ | isobutyl, X₄ | 40° C. | 1.54(D) | 514.6 |
| 32 | naphthalen-2-ylsulfonyl-X₁ | -CH₂CH₂COOH, X₂ | H-X₂ₐ | isobutyl, X₃ | isobutyl, X₄ | 40° C. | 1.61(D) | 530.5 |
| 33 | 4-chlorophenylsulfonyl-X₁ | -CH₂CH₂COOH, X₂ | H-X₂ₐ | isobutyl, X₃ | -CH₂CH₂COOH, X₄ | 40° C. | 1.21(D) | 529.4 |
| 34 | naphthalen-2-ylsulfonyl-X₁ | -CH₂CH₂COOH, X₂ | H-X₂ₐ | isobutyl, X₃ | -CH₂CH₂COOH, X₄ | 40° C. | 1.27(D) | 546.4 |
| 35 | 4-chlorophenylsulfonyl-X₁ | -CH₂CH₂COOH, X₂ | H-X₂ₐ | sec-butyl, X₃ | isobutyl, X₄ | 40° C. | 1.57(D) | 513.4 |

TABLE 2-continued

REPRESENTATIVE COMPOUNDS)

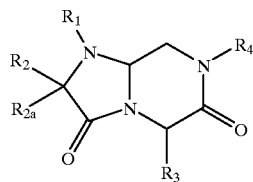

| Cpd. No. | R₁ | R₂ | R₂ₐ | R₃ | R₄ | Cleavage Conditions | LC RT‡ (min) | MS (M + H⁺) |
|---|---|---|---|---|---|---|---|---|
| 36 | naphthyl-SO₂-X₁ | HOOC-CH₂-CH(X₂)- (iiii) | H-X₂ₐ | (S)-sec-butyl (X₃) | isobutyl (X₄) | 40° C. (48 h) | 1.62(D) | 530.5 |
| 37 | 4-Cl-C₆H₄-SO₂-X₁ | HOOC-CH₂-CH(X₂)- | H-X₂ₐ | (S)-sec-butyl (X₃) | HOOC-CH₂-CH₂-X₄ | 40° C. | 1.20(D) | 529.3 |
| 38 | naphthyl-SO₂-X₁ | HOOC-CH₂-CH(X₂)- | H-X₂ₐ | (S)-sec-butyl (X₃) | HOOC-CH₂-CH₂-X₄ | 40° C. | 1.27(D) | 546.5 |
| 39 | 4-Cl-C₆H₄-SO₂-X₁ | HOOC-CH₂-CH(X₂)- | H-X₂ₐ | benzyl (X₃) | isobutyl (X₄) | 40° C. | 1.60(D) | 547.3 |
| 40 | naphthyl-SO₂-X₁ | HOOC-CH₂-CH(X₂)- | H-X₂ₐ | benzyl (X₃) | isobutyl (X₄) | 40° C. | 1.64(D) | 564.5 |
| 41 | 4-Cl-C₆H₄-SO₂-X₁ | HOOC-CH₂-CH(X₂)- | H-X₂ₐ | benzyl (X₃) | HOOC-CH₂-CH₂-X₄ | 40° C. | 1.22(D) | 563.4 |
| 42 | naphthyl-SO₂-X₁ | HOOC-CH₂-CH(X₂)- | H-X₂ₐ | benzyl (X₃) | HOOC-CH₂-CH₂-X₄ | 40° C. | 1.28(D) | 580.5 |

TABLE 2-continued

REPRESENTATIVE COMPOUNDS)

| Cpd. No. | $R_1$ | $R_2$ | $R_{2a}$ | $R_3$ | $R_4$ | Cleavage Conditions | LC RT‡ (min) | MS (M + H$^+$) |
|---|---|---|---|---|---|---|---|---|
| 43 | 4-Cl-C$_6$H$_4$-SO$_2$-X$_1$ | HOOC-CH$_2$-CH(X$_2$)- | H-X$_{2a}$ | X$_3$-CH(4-F-C$_6$H$_4$)- | (CH$_3$)$_2$CH-CH$_2$-X$_4$ | 40° C. | 1.60(D) | 565.4 |
| 44 | 2-naphthyl-SO$_2$-X$_1$ | HOOC-CH$_2$-CH(X$_2$)- | H-X$_{2a}$ | X$_3$-CH(4-F-C$_6$H$_4$)- | (CH$_3$)$_2$CH-CH$_2$-X$_4$ | 40° C. | 1.65(D) | 582.5 |
| 45 | 4-Cl-C$_6$H$_4$-SO$_2$-X$_1$ | HOOC-CH$_2$-CH(X$_2$)- | H-X$_{2a}$ | X$_3$-CH(4-F-C$_6$H$_4$)- | HOOC-CH$_2$-CH$_2$-X$_4$ | 40° C. | 1.25(D) | 581.4 |
| 46 | 2-naphthyl-SO$_2$-X$_1$ | HOOC-CH$_2$-CH(X$_2$)- | H-X$_{2a}$ | X$_3$-CH(4-F-C$_6$H$_4$)- | HOOC-CH$_2$-CH$_2$-X$_4$ | 40° C. | 1.30(D) | 598.5 |
| 47 | 2-naphthyl-SO$_2$-X$_1$ | HOOC-CH$_2$-CH(X$_2$)- | H-X$_{2a}$ | X$_3$-CH(C$_6$H$_5$)- | CH$_3$-CH$_2$-CH$_2$-CH$_2$-X$_4$ | 40° C. | 1.65(D) | 564.5 |
| 48 | 2-naphthyl-SO$_2$-X$_1$ | HOOC-CH$_2$-CH(X$_2$)- | H-X$_{2a}$ | X$_3$-CH(C$_6$H$_5$)- | C$_6$H$_5$-CH$_2$-CH$_2$-X$_4$ | 40° C. | 1.70(D) | 612.4 |
| 49 | 2-naphthyl-SO$_2$-X$_1$ | HOOC-CH$_2$-CH(X$_2$)- | H-X$_{2a}$ | X$_3$-CH(C$_6$H$_5$)- | 2-pyridyl-CH$_2$-X$_4$ | 60° C. (48 h) | 1.47(D) | 599.4 |

TABLE 2-continued

REPRESENTATIVE COMPOUNDS)

| Cpd. No. | R$_1$ | R$_2$ | R$_{2a}$ | R$_3$ | R$_4$ | Cleavage Conditions | LC RT‡ (min) | MS (M + H$^+$) |
|---|---|---|---|---|---|---|---|---|
| 50 | naphthalen-2-ylsulfonyl (X$_1$) | –CH$_2$–COOH (X$_2$) | H (X$_{2a}$) | benzyl (X$_3$) | –CH$_2$CH$_2$–S(O)$_2$–Ph (X$_4$) | 40° C. | 1.53(D) | 676.5 |
| 51 | naphthalen-2-ylsulfonyl (X$_1$) | –CH$_2$–COOH (X$_2$) | H (X$_{2a}$) | benzyl (X$_3$) | –CH$_2$CH$_2$–Ph (X$_4$) | 40° C. | 1.68(D) | 612.4 |
| 52 | naphthalen-2-ylsulfonyl (X$_1$) | –CH$_2$–COOH (X$_2$) | H (X$_{2a}$) | benzyl (X$_3$) | –CH$_2$CH$_2$–Ph (X$_4$) | 40° C. | 1.71(D) | 612.4 |
| 53 | naphthalen-2-ylsulfonyl (X$_1$) | –CH$_2$–COOH (X$_2$) | H (X$_{2a}$) | benzyl (X$_3$) | –CH$_2$CH$_2$–Ph (X$_4$) | 40° C. | 1.65(D) | 612.4 |
| 54 | 8-chloronaphthalen-2-ylsulfonyl (X$_1$) | –CH$_2$–COOH (X$_2$) | H (X$_{2a}$) | benzyl (X$_3$) | –CH$_2$CH$_2$–COOH (X$_4$) | 40° C. | 1.40(D) | 614.3 |
| 55 | naphthalen-2-ylsulfonyl (X$_1$) | –CH$_2$–COOH (X$_2$) | H (X$_{2a}$) | benzyl (X$_3$) | –CH$_2$CH$_2$–CH(CH$_3$)$_2$ (X$_4$) | 40° C. | 1.70(D) | 578.3 |

‡LCMS analysis was performed on reverse-phase C$_{18}$ Zorbax columns using the following solvent system: A, water with 0.1% formic acid; B, acetonitrile with 0.1% formic acid. The following conditions were applied: (A), column 2.1 × 30 mm, 5–95% B in 4 min, flow 0.3 ml/min; (B), column 4.6 × 100 mm, 5–90% B in 15 min, flow 1.5 ml/min; (C), column 2.1 × 30 mm, 5–95% B in 3 min, flow 0.5 ml/min; (D), column 2.1 × 30 mm, 5–95% B in 2 min, flow 0.8 ml/min. Mass spectra for separated peaks were obtained either by electrospray (ES) or by atmospheric pressure chemical ionization (APCI) using a MicroMass LCZ mass spectrometer with the appropriate probes.

Example 2

Biological Activity of Representative Compounds

An assay measuring the ability of the compounds of Example 1 to antagonize binding of CS1 peptide to $\alpha_4\beta_1$ integrin was performed. A modification of the procedure of Vanderslice, P. et al. (*J Immunol.*, 1997, 1710–1718) (incorporated herein by reference) was utilized.

In brief, 100 μL/well of a solution of biotinylated CS1 peptide (1 mg/100 mL of phosphate buffered saline (PBS)) was incubated in a NeutrAvidin plate (Pierce) for 1 h at room temperature. The plate was then washed 3× with distilled water and treated with 200 μL of blocking buffer (3% BSA in PBS) for at least 4 h. Blocked plates were washed as above. Harvested Ramos cells ($10^7$/mL) were resuspended in PBS containing 10 μL of calcein AM/mL and incubated 30 min in the dark. This suspension was diluted with 45 mL PBS and the cells harvested by centrifugation and aspiration. The cells were resuspended in binding buffer (~$5 \times 10^5$/mL). If cell lysis was to be monitored ethidium homodimer was added to the buffer to a final concentration of 5 μM. A solution (10 μL) of compound to be tested or control peptide was added to appropriate wells followed by 90 μL of the cell suspension. The plate was incubated at 37° C. for 1 h. When ethidium homodimer was added, fluorescence at 535/617 was measured before rinsing. Otherwise, the plate was washed 3×, 50 μL of lysis buffer was added to each well, the plate rocked in the dark for 10 min, and the fluorescence monitored at 485 nm excitation and 535 nm emission.

Preferably, the compounds of this invention have an $IC_{50}$ value of less than 100 μM in this assay. To this end, preferred compounds of this invention are compounds 4, 5, 8–10, 31, 32, 38–49, 54 and 55, and more preferred compounds having an $IC_{50}$ value of less than 10 μM are compounds 10, 41, 42, 44–49, 54 and 55. As such, the compounds of this invention effectively inhibit cell adhesion and possess activity as anti-inflammatory agents.

It will be appreciated that, although specific embodiments of the invention have been described herein for the purposes of illustration, various modifications may be made without departing from the spirit and scope of the invention. Accordingly, the invention is not limited except by the appended claims.

We claim:

1. A compound having the structure:

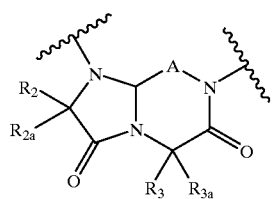

or a pharmaceutically acceptable salt or stereoisomer thereof,
wherein
A is —$(CR_5R_{5a})_n$— where n is 1, 2 or 3;
$R_2$, $R_3$ and $R_5$ are, at each occurrence, the same or different and independently an amino acid side chain moiety or amino acid side chain derivative, a peptide or peptide derivative, a linker or a solid support; and
$R_{2a}$, $R_{3a}$ and $R_{5a}$ are, at each occurrence, the same or different and independently hydrogen, hydroxy, —COOH, —$CONH_2$, —$R_6$, —$OR_6$, —$COOR_6$, —$COR_6$ or —$CONHR_6$, where $R_6$ is lower alkyl optionally substituted with halogen or hydroxy;
with the proviso that the compound is not methyl (2R,5S,8aS)-7-benzyl-2-isopropyl-5-methyl-3,6-dioxohexahydro-imidazo[1,2a]pyrazine-1(5H)-carboxylate or methyl (2S,5S,8aS)-7-benzyl-5-isopropyl-2-methyl-3,6-dioxohexahydroimidazo[1,2-a]pyrazine-1(5H)-carboxylate.

2. The compound of claim 1 wherein $R_{2a}$ and $R_{3a}$ are hydrogen, and the compound has the structure:

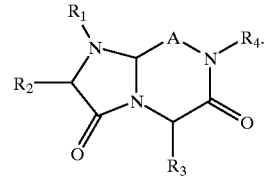

3. The compound of claim 2 wherein n is 1, $R_{5a}$ is hydrogen, and the compound has the structure:

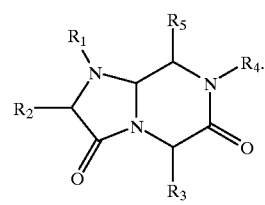

4. The compound of claim 3 wherein $R_5$ is hydrogen.

5. The compound of claim 2 wherein n is 2, $R_{5a}$ is hydrogen at each occurrence, and the compound has the structure:

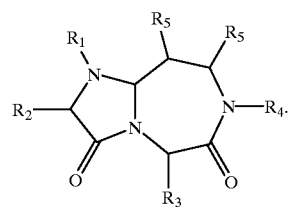

6. The compound of claim 5 wherein $R_5$ is hydrogen at each occurrence, and the compound has the structure:

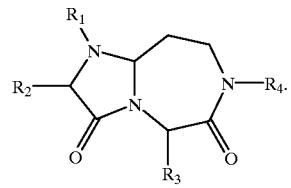

7. The compound of claim 1 wherein $R_{3a}$ is hydrogen, and the compound has the structure:

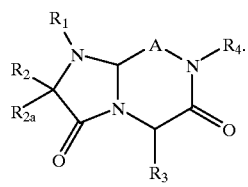

8. The compound of claim 2 or 7 wherein $R_2$, $R_3$ and $R_4$ are the same or different and are independently an amino acid side chain moiety or an amino acid side chain derivative.

9. The compound of claim 1 wherein $R_1$ is —C(=O)OR$_7$, —C(=O)NHR$_7$ or —SO$_2$R$_7$ where $R_7$ is an amino acid side chain moiety or an amino acid side chain derivative.

10. The compound of claim 9 wherein $R_7$ aryl or arylalkyl optionally substituted with halogen, —OH, —COOH, —NH$_2$ or alkyl.

11. The compound of claim 9 wherein $R_{2a}$ and $R_{3a}$ are hydrogen.

12. The compound of claim 9 wherein $R_2$ is —(CH$_2$)$_2$COOH.

13. The compound of claim 9 wherein $R_3$ is benzyl or substituted benzyl.

14. The compound of claim 9 wherein $R_1$ is —SO$_2$R$_7$.

15. The compound of claim 14 wherein the compound has the structure:

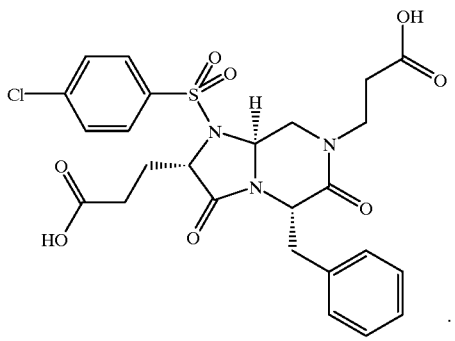

16. The compound of claim 14 wherein the compound has the structure:

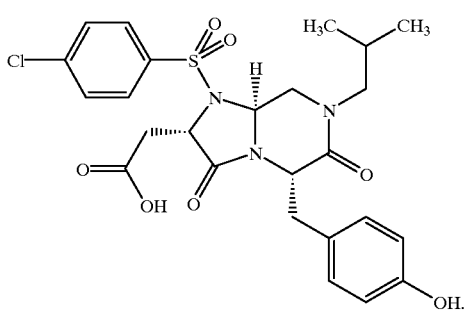

17. The compound of claim 14 wherein the compound has the structure:

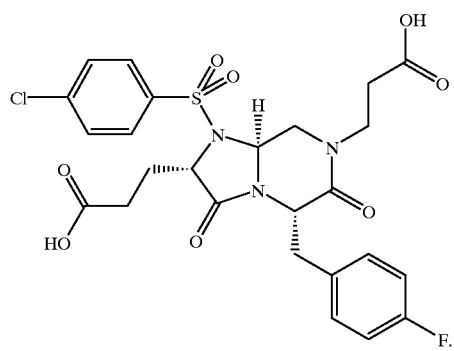

18. The compound of claim 14 wherein the compound has the structure:

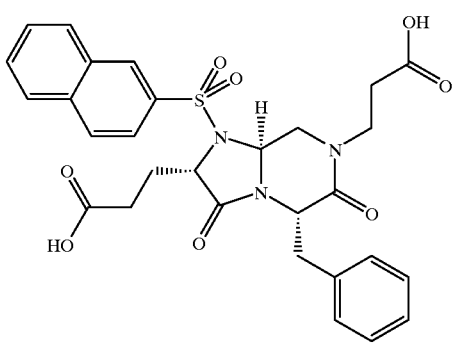

19. The compound of claim 14 wherein the compound has the structure:

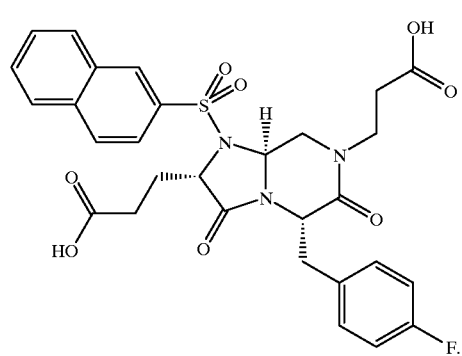

20. The compound of claim 14 wherein the compound has the structure:

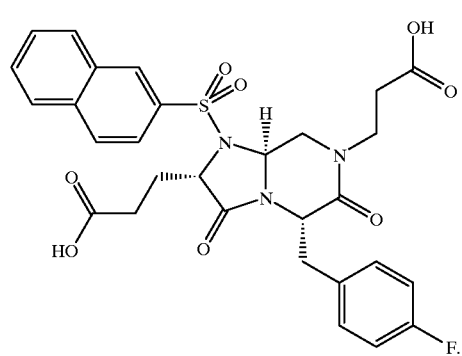

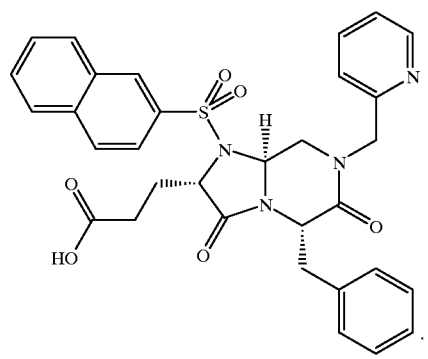
21. The compound of claim 14 wherein the compound has the structure:
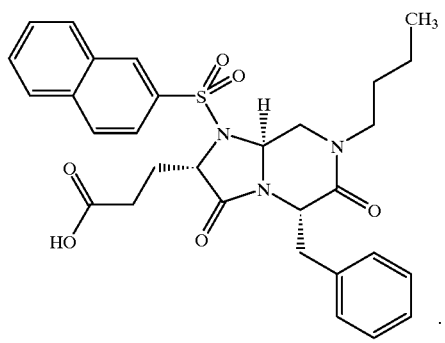
22. The compound of claim 14 wherein the compound has the structure:
23. The compound of claim 14 wherein the compound has the structure:
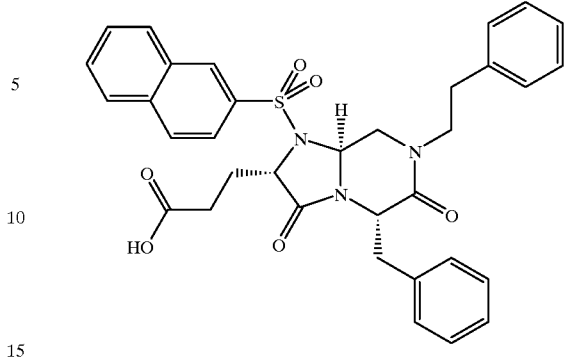
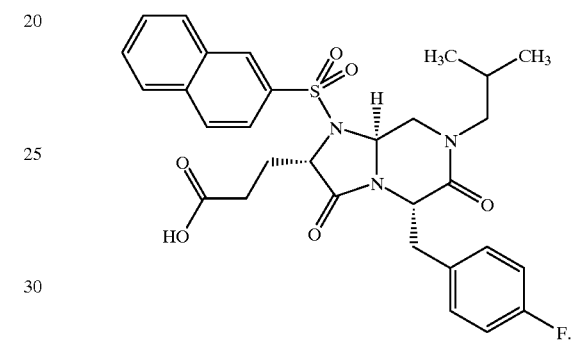
24. A composition comprising a compound of claim 1 and a pharmaceutically acceptable carrier.
* * * * *